United States Patent [19]

Chiang et al.

[11] Patent Number: 5,550,238

[45] Date of Patent: Aug. 27, 1996

[54] PROCESS FOR PREPARING SULFONYLUREAS

[75] Inventors: George C. Chiang, Wilmington; Richard F. Davis, Newark; Kwaku O. Temeng, Wilmington, all of Del.

[73] Assignee: E. I. Du Pont de Nemours and Company, Wilmington, Del.

[21] Appl. No.: 518,435

[22] Filed: Aug. 23, 1995

[51] Int. Cl.$^6$ ............... C07D 251/42; C07D 251/48; C07D 239/42; C07D 239/48

[52] U.S. Cl. ............ 544/211; 544/206; 544/208; 544/321; 544/323; 544/332

[58] Field of Search ................ 544/211, 206, 544/208, 321, 323, 332

[56] References Cited

U.S. PATENT DOCUMENTS

| | | | |
|---|---|---|---|
| 4,546,179 | 10/1985 | Kunz | 544/206 |
| 5,157,119 | 10/1992 | Campopiano et al. | 544/211 |
| 5,480,993 | 1/1996 | Choi et al. | 544/320 |

*Primary Examiner*—John M. Ford

[57] ABSTRACT

This invention relates to a process for preparing sulfonylureas comprising reacting a sulfonyl chloride with a cyanate salt and an amine base in the presence of an inert aprotic solvent to give an isocyanate complex which is then reacted with an amino heterocycle to form the sulfonylurea product and a process for converting the crystal form of the prepared sulfonylurea product to a more stable crystal product form.

10 Claims, No Drawings

PROCESS FOR PREPARING SULFONYLUREAS

BACKGROUND OF THE INVENTION

This invention is directed to the preparation of an isocyanate complex which is further reacted by coupling with an aminoheterocycle and the product processed to convert one crystal form of the resultant sulfonylurea product to a more stable crystal product form.

There is a continuing need to discover new processes for the preparation of the highly active sulfonylurea class of compounds where the preparation offers distinct advantages that add to their desirability. Already known in the art are U.S. Pat. Nos. 4,546,179 and 5,157,119 that pertain to a process to prepare sulfonylureas. The purity and crystal form obtained by these processes may not be acceptable for formulation development.

SUMMARY OF THE INVENTION

This invention pertains to a process for the preparation of sulfonylureas of Formula I comprising reacting a sulfonyl chloride of Formula II with a cyanate salt of Formula III and an amine base of Formula IV to give an isocyanate complex of Formula V, which is then reacted with an aminoheterocycle of Formula VI according to Equations 1 and 2.

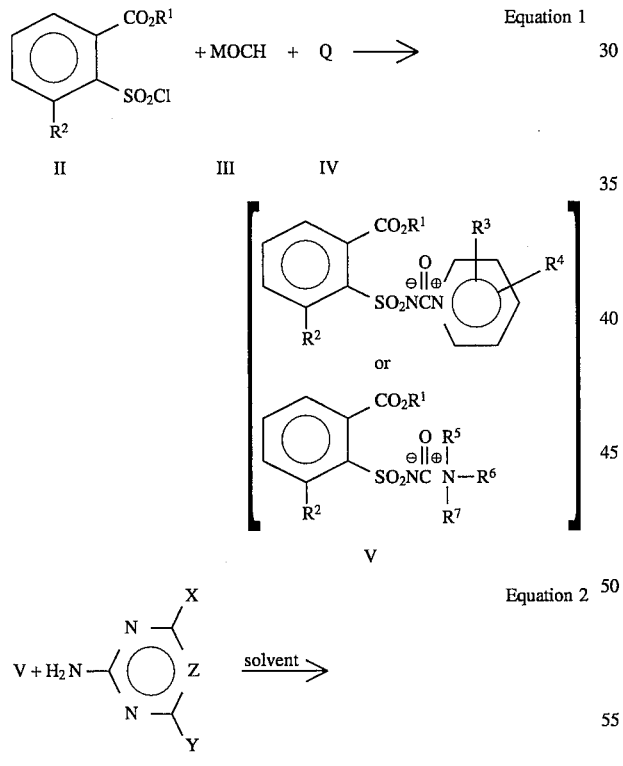

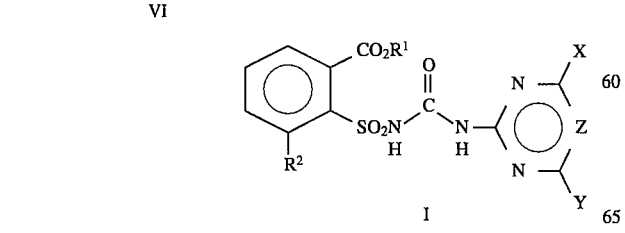

wherein:

$R^1$ is $C_1$-$C_4$ alkyl;
$R^2$ is $C_1$-$C_2$ alkyl or $C_1$-$C_2$ haloalkyl;
$R^3$ is H, $C_1$-$C_2$ alkyl, Br, or Cl;
$R^4$ is H, $C_1$-$C_2$ alkyl, Br, or Cl;
$R^3$ and $R^4$ can also be taken together to form an aromatic ring where the structure becomes quinoline or isoquinoline.
M is Na or K;
X $CH_3$ or $N(CH_3)_2$;
Y is $CH_3$, $OCH_3$ or $OCH_2CF_3$;
Z is CH or N;
Q is $Q_1$ or $Q_2$;
$Q_1$ is

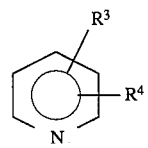

$Q_2$ is

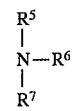

$R^5$, $R^6$, and $R^7$ are each independently $C_1$-$C_3$ alkyl, phenyl or benzyl;
$R^5$ and $R^6$ can be taken together as —$CH_2CH_2$ A $CH_2CH_2$— or —$CH_2CH_2CH_2CH_2$—;
or $R^5$, $R^6$, $R^7$ can be taken together as

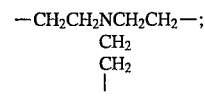

A is O, $NR^8$; and
$R^8$ is $C_1$-$C_3$ alkyl.

The process of this invention is advantageous as it allows for the production of sulfonylureas via an isocyanate complex often in high yields under moderate reaction conditions and, in addition, allows for conversion of the resultant product to a more stable or desired crystal form for formulation development.

The process for the conversion to a more stable crystal form of the sulfonylureas of Formula I is achieved by treating the solids with appropriate solvents.

Thus, the process of the invention involves the preparation of a sulfonylurea of Formula I

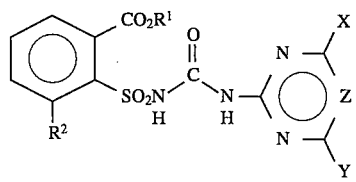

wherein:
$R^1$ is $C_1$-$C_4$ alkyl;
$R^2$ is $C_1$-$C_2$ alkyl or $C_1$-$C_2$ haloalkyl;
X $CH_3$ or $N(CH_3)_2$;
Y is $CH_3$, $OCH_3$ or $OCH_2CF_3$;

Z is CH or N;
comprising reacting the sulfonyl chloride of Formula II

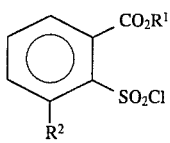

wherein $R^1$ and $R^2$ are as defined above
with a cyanate salt of the Formula III

MOCN   III wherein M is Na or K
in the presence of an inert aprotic solvent and heterocyclic amine base of the Formula IV

Q

IV wherein Q is $Q_1$ or $Q_2$ $Q_1$ is

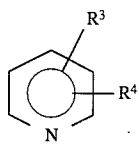

$Q_2$ is

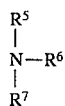

$R^3$ is H, $C_1$-$C_2$ alkyl, Br, or Cl;

$R^4$ is H, $C_1$-$C_2$ alkyl, Br, or Cl;

$R^3$ and $R^4$ can also be taken together to form an aromatic ring where the structure becomes quinoline or isoquinoline;

$R^5$, $R^6$, and $R^7$ are each independently $C_1$-$C_3$ alkenyl, phenyl or benzyl;

$R^5$ and $R^6$ can be taken together as —$CH_2CH_2$ A $CH_2CH_2$— or —$CH_2CH_2CH_2CH_2$—;

or $R^5$, $R^6$, $R^7$ can be taken together as

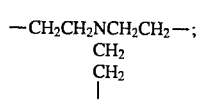

A is O, $NR^8$; and $R^8$ is $C_1$-$C_3$ alkyl at a temperature of 0° to 60° C. and a pressure of 1 to 5 atmospheres for a time sufficient to give an isocyanate complex of the Formula V

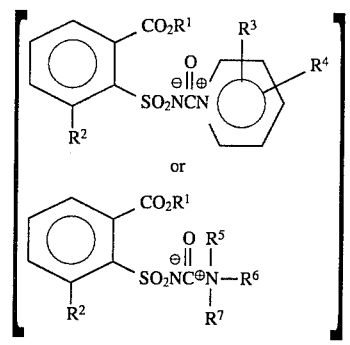

wherein $R^1$, $R^2$, $R^3$, $R^4$, $R^5$, $R^6$ and $R^7$ are as defined above;
which is then reacted with an aminoheterocycle of Formula VI

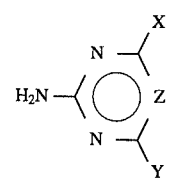

wherein X, Y and Z are as defined above.
in the presence of an inert aprotic solvent at a temperature of 0° to 50° C. and a pressure of 1 to 5 atmospheres for a time sufficient to yield the sulfonylurea of Formula I.

Typical reaction conditions are as follows. The solvent in Equations 1 and 2 are selected from inert aprotic solvents with preferred solvents selected from acetonitrile, acetone, dioxane, methylene chloride, tetrahydrofuran and suitable combinations thereof. Temperatures are 0° to 60° C. for the complex formation step of Equation 1 and 0° to 50° C. for the coupling step of Equation 2. Preferred temperatures are 15° to 35° C. for both steps. Reaction pressures are 1 to 5 atmospheres for both steps. The preferred pressure is 1 atmosphere for both steps. Reaction times are 0.1 to 24 hours for the complex formation step, preferably 2–6 hours, and 0.1 to 10 hours for the coupling step, preferably 0.2–1.5 hours. The amine base may be a heterocyclic amine or a tertiary amine. Preferably the amine is selected from the group consisting of pyridine, picoline, lutidine or triethylamine, N,N diethylaniline, 4-methyl morpholine and tribenzylamine. The most preferred amine is pyridine. Preferred mole ratio of the compound of Formula II to amine base is 1:2 to 1:3. Solvents for the conversion of crystal forms can be chosen from alcohols, carboxylic acids, nitriles, ketones, aldehydes, aliphatic hydrocarbons aromatic hydrocarbons, alicyclic hydrocarbons, amides, alkanes, alkyl halides, ethers, esters, water and appropriate combinations thereof. Preferred solvents include methanol, acetic acid, acetonitrile, acetone, xylene, and water or suitable combinations. Temperatures for conversion of crystal forms are 0° to 50° C., preferably 10° to 30° C., and the solvent can be in either the liquid or vapor phase.

The preferred processes of the invention are those that produce the products indicated below:

1) The process of Equation 1 wherein $R^1$ is $CH_3$, $R^2$ is $CH_3$, Q is pyridine, the solvent is acetonitrile, the reaction temperature is 15°–35° C., the pressure is 1 atmosphere, reaction time is 2 to 6 hours and the mole ratio of the compound of Formula II to amine base is 1:2 to 1:3.

2) The process of Equation 2 wherein $R^1$ is $CH_3$, $R^2$ is $CH_3$, Q is pyridine, Z is N, X is $N(CH_3)_2$, Y is OCH$_2$CF$_3$, the solvent is acetonitrile, the reaction temperature is 15°–35° C., the pressure is 1 atmosphere, and the reaction time is 0.2 to 1.5 hours.

3) The process of conversion of crystal forms for products of Formula I wherein R$^1$ is CH$_3$, R$^2$ is CH$_3$, Z is N, X is N(CH$_3$)$_2$, Y is OCH$_2$CF$_3$, the solvent is methanol, and the wetcake temperature is 10° to 30° C.

DESCRIPTION OF THE INVENTION

The sulfonyl chlorides of Formula II are either known or can be prepared by various methods known to one skilled in the art. For example, the compounds of Formula II can be prepared by i) oxidative chlorination of thioethers such as taught in *Recl. Trav. Chim. Pays-Bas* 101, 91 (1982), ii) diazotization of aromatic amines with sodium nitrite in hydrochloric acid, followed by reaction of the resulting diazonium salt with sulfur dioxide and cuprous chloride as described in *J. Org. Chem.*, 1824 (1960), or iii) heteroatom-facilitated lithiation, followed by sulfonation as taught in EPA-73,562 and reviewed in *Org. Reactions*, 26, 1 (1979), and v) Newman rearrangement followed by oxidative chlorination as taught by U.S. Pat. No. 5,157,119.

The aminoheterocycles of Formula VI are also either known or can be prepared by methods known in the art. For example, see "The Chemistry of Heterocyclic Compounds," Vol. 13 and 16, Interscience Publishers, Inc., New York and "The Chemistry of the Amino Group," Edited by S. Patai, Interscience Publishers, Inc., pages 37–77.

The process for the preparation of the complex V is generally carried out in an inert aprotic solvent. The preferred solvents are selected from acetonitrile, dioxane, methylene chloride, tetrahydrofuran, or combinations thereof. The preferred solvent for greater reactivity and ease of handling is acetonitrile.

The cyanate salts III are sodium or potassium.

The reaction temperature is in the range of 0° to 60° C. for the formation of complex V and 0° to 50° C. for the reaction with amino heterocycle VI, with ambient temperature preferred for ease of operation for both steps. The reaction pressure is 1 to 5 atmospheres, with 1 atmosphere preferred for each step.

The reaction time for the complex formation of the complex V is determined by the reactivity of the starting materials. In some cases, the reaction is complete after a few minutes while in other cases a reaction time up to about 24 hours is advantageous. The preferred reaction time is normally in the range of 2 to 6 hours.

The reaction time for the coupling reaction involving Formula VI is determined by the reactivity of the starting materials and by the formation of side products. In many cases the reaction is complete after a few minutes while in other cases a couple of hours may be desired. The preferred reaction time is normally in the range of 0.2 to 1.5 hour.

The relative ratio of reactants is determined by their relative cases and reactivity. The cyanate salt is used in excess. Mole ratios of sulfonyl chloride to cyanate salt can be 1:1 to 1:10 with preferred 1:1.5 to 1:2 for reasons of ease of operation and efficiency.

The mole ratio of sulfonyl chloride to amine base is generally 1:0.5 to 1:3, with 1:2 to 1:3 preferred. An excess of amine is preferred for increased rate of reaction and to ensure that complex formation goes to completion. The preferred amine bases are selected from heterocyclic amines or tertiary amines, with pyridine as the preferred amine.

The sulfonyl chloride II and the aminoheterocycle VI are generally used in a 1:1 to 1.5:1 ratio, with the preferred ratio in the range of 1.2:1 to 1.4:1. It is desirable to have the sulfonyl chloride and the resultant isocyanate complex in excess in order to ensure complete reaction of the aminoheterocycle.

The resulting sulfonylurea product I is isolated by several methods depending on the solvent, the solubility of the product and the presence of by-products. In some cases, the reaction can be acidified, diluted with water and filtered to give essentially pure sulfonylurea. In other cases the product can be dissolved in dilute base, filtered, and the filtrate acidified to reprecipitate the product. In still other cases, the product is recrystallized to yield purified product. When desired for stability or ease of handling, the crystal form of the product sulfonylurea may be modified by washing or slurrying in common solvents. Representative examples include solvents from the classes of alcohols, carboxylic acids, nitriles, ketones, aldehydes, aliphatic hydrocarbons, aromatic hydrocarbons, alicyclic hydrocarbons, amides, alkanes, alkyl halides, ethers, esters and water or suitable combinations. Preferred solvents would include methanol, acetic acid, acetonitrile, acetone, xylene, water, or suitable combinations thereof. For ease of operation and drying, washing of the product wet cake with methanol to convert to more stable crystal form is the most preferred solvent. One skilled in the art would be able to select between solvent combinations based on physical properties like solubility of the sulfonylurea.

The process of this invention is further illustrated by the following examples.

EXAMPLE 1

Preparation of Methyl 2-[[[[[4-(dimethylamino)- 6-(2,2,2-trifluoroethoxy)-1,3,5-triazin-2yl]amino]carbonyl]amino]sulfonyll-3-methylbenzoate To a stirred mixture of 16.5 g (0.25 mole) of sodium cyanate and 38.0 g (0.15 mole) of methyl 2-(chlorosulfonyl)-3-methylbenzoate in 150 mL of acetonitrile was added 30 mL (0.37 mole) of pyridine. Upon the addition of the pyridine an endotherm occurred, followed by a mild exotherm. A cooling bath was used to maintain the reactor temperature at 20°–25° C. while the reaction mixture was stirred for 4 hours. 27.0 g (0.11 mole) of 4-(dimethylamino)-6-(2,2,2-trifluoroethoxy)-1,3,5-triazin-2-amine was added all at once to the reaction mixture, and the reaction mixture was stirred for 0.5 h. 120 mL of 70% acetic acid was rapidly added to the reaction mixture, followed by the slow addition of 280 mL of water over 0.5 h. The solids were collected by filtration and the filter cake washed with 100 mL of water, followed by two 30 mL methanol washes to displace the water from the cake. The solid was dried overnight in a vacuum oven at 60° C. to yield 49.3 g of a white solid (85%), mp 160°–162° C. The purity of the product was determined by liquid chromatography to be 98.5 area %.

EXAMPLE 2

Crystal conversion of Methyl 2-[[[[[4-(dimethylamino)-6-(2,2,2-trifluoroethoxy)-1,3,5-triazin-2-yl]amino]carbonyl]amino]sulfonyl]-3-methylbenzoate.

A slurry of 10.0 g of the alpha crystal form of Example 1 (mp 102°–108° C.) in 23.3 g of methanol was stirred at 22° C. for 2 h. The solids were collected by filtration and dried in a vacuum oven to yield 9.2 g of Example 1 in the beta crystal form, mp 162°–164° C.

What is claimed is:

1. A process for the preparation of a sulfonylurea of the formula:

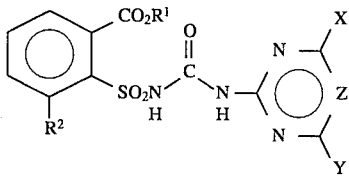

I wherein:

$R^1$ is $C_1$-$C_4$ alkyl;
$R^2$ is $C_1$-$C_2$ alkyl or $C_1$-$C_2$ haloalkyl;
X $CH_3$ or $N(CH_3)_2$;
Y is $CH_3$, $OCH_3$ or $OCH_2CF_3$;
Z is CH or N;

comprising reacting the sulfonyl chloride of Formula II

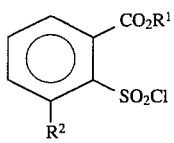

II wherein $R^1$ and $R^2$ are as defined above with a cyanate salt of the Formula III

MOCN     III wherein M is Na or K
in the presence of an inert aprotic solvent and a heterocyclic amine base of the Formula IV

Q

IV wherein Q is $Q_1$ or $Q_2$ $Q_1$ is

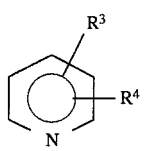

$Q_2$ is

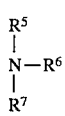

at a temperature of 0° to 60° C. and a pressure of 1 to 5 atmospheres for a time sufficient to give an isocyanate complex of the Formula V

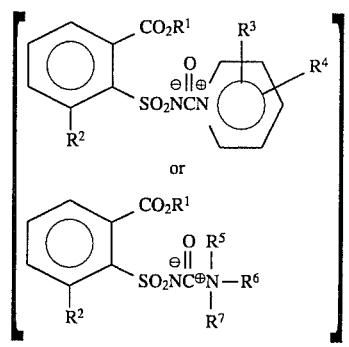

V wherein $R^1$ and $R^2$ are as defined above;

$R^3$ is H, $C_1$-$C_2$ alkyl, Br, or Cl;
$R^4$ is H, $C_1$-$C_2$ alkyl, Br, or Cl;
$R^3$ and $R^4$ can also be taken together to form an aromatic ring where the structure becomes quinoline or isoquinoline;
$R^5$, $R^6$, and $R^7$ are each independently $C_1$-$C_3$ alkenyl, phenyl or benzyl;
$R^5$ and $R^6$ can be taken together as —$CH_2CH_2$ A $CH_2CH_2$— or —$CH_2CH_2CH_2CH_2$—;
or $R^5$, $R^6$, $R^7$ can be taken together as

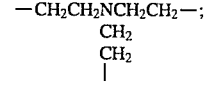

A is 0, $NR^8$; and
$R^8$ is $C_1$-$C_3$ alkyl which is then reacted with an aminoheterocycle of Formula VI

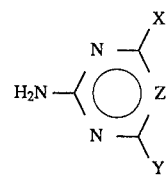

VI wherein X, Y and Z are as defined above.
in the presence of an inert aprotic solvent at a temperature of 0° to 50° C. and a pressure of 1 to 5 atmospheres for a time sufficient to yield the sulfonylurea of Formula I.

2. The process of claim 1 wherein the sulfonylurea product of Formula I is treated with a solvent at a temperature 0° to 50° C. to convert the crystal form of the sulfonylurea of Formula I to a more stable crystal form.

3. The process of claim 1 wherein the inert aprotic solvent used to prepare the isocyanate complex is selected from acetonitrile, acetone, dioxane, methylene chloride, tetrahydrofuran and combinations thereof.

4. The process of claim 1 wherein the amine base is selected from pyridine, picoline, lutidine, triethylamine, N,N-diethylaniline, 4-methyl morpholine, tribenzylamine.

5. The process of claim 1 wherein the temperature is 15° to 35° C. and the pressure is 1 atmosphere for the preparation of the complex of Formula V.

6. The process of claim 2 wherein the solvent for converting the crystal form is selected from methanol, acetic acid, acetonitrile, acetone, xylene, water or suitable combination thereof.

7. The process of claim 1 wherein $R^1$ is $CH_3$, $R^2$ is $CH_3$, Q is pyridine, the inert aprotic solvent is acetonitrile, the reaction temperature is 15°–35° C. and the pressure is 1 atmosphere.

8. The process of claim 1 wherein $R^1$ is $CH_3$, $R^2$ is $CH_3$, Q is pyridine, Z is N, X is $N(CH_3)_2$, Y is $OCH_2CF_3$, and the inert aprotic solvent in both instances is acetonitrile.

9. The process of claim 2 wherein the solvent is methanol.

10. The process of claim 2 wherein $R^1$ is $CH_3$, $R^2$ is $CH_3$, Z is N, X is $N(CH_3)_2$, Y is $OCH_2CF_3$, the solvent for converting the crystal form is methanol and the temperature is 10° to 30° C.

* * * * *